US009700458B2

(12) United States Patent
Giardina et al.

(10) Patent No.: US 9,700,458 B2
(45) Date of Patent: Jul. 11, 2017

(54) APPARATUS AND DIAMOND BLADE MECHANISM TO MAKE AN ANNULAR INCISION IN SOFT TISSUE

(71) Applicant: Rhexis Surgical Instruments, Inc., Chapel Hill, NC (US)

(72) Inventors: Christopher Kenneth Giardina, Chapel Hill, NC (US); Shane Anthony Saunders, Roswell, GA (US); Khaled Nizar Kashlan, Suwanee, GA (US); Rebeca Kyker Bowden, Seattle, WA (US); Jorge Alejandro Baro, Lawrenceville, GA (US); Kanitha Kim Mann, Atlanta, GA (US)

(73) Assignee: Rhexis Surgical Instruments, Inc., Chapel Hill, NC (US)

(*) Notice: Subject to any disclaimer, the term of this patent is extended or adjusted under 35 U.S.C. 154(b) by 132 days.

(21) Appl. No.: 14/706,408

(22) Filed: May 7, 2015

(65) Prior Publication Data

US 2015/0238359 A1  Aug. 27, 2015

Related U.S. Application Data

(63) Continuation-in-part of application No. 13/415,035, filed on Mar. 8, 2012, now abandoned.

(60) Provisional application No. 61/450,389, filed on Mar. 8, 2011.

(51) Int. Cl.
*A61F 9/007* (2006.01)
*A61B 17/3205* (2006.01)

(52) U.S. Cl.
CPC .... *A61F 9/00763* (2013.01); *A61B 17/32053* (2013.01); *A61F 9/00754* (2013.01)

(58) Field of Classification Search
CPC .. A61F 9/00754; A61F 9/00763; A61F 9/007; A61F 9/00736; A61B 17/320758; A61B 17/32053
See application file for complete search history.

(56) References Cited

U.S. PATENT DOCUMENTS

| 3,976,077 | A | 8/1976 | Kerfoot, Jr. |
| 4,061,146 | A | 12/1977 | Baehr et al. |
| 4,367,744 | A | 1/1983 | Sole |
| 4,708,138 | A | 11/1987 | Pazandak |
| 4,805,616 | A | 2/1989 | Pao |
| 4,911,161 | A | 3/1990 | Schechter |
| 5,261,923 | A | 11/1993 | Soares |
| 5,269,787 | A | 12/1993 | Cozean, Jr. et al. |
| 5,328,484 | A | 7/1994 | Somers et al. |
| 5,346,491 | A | 9/1994 | Oertli |

(Continued)

OTHER PUBLICATIONS

Fisher, "The Significance of the Shape of the Lens and Capsular Energy Changes in Accommodation", J. Physiol., 201, pp. 21-47, 1969.

(Continued)

*Primary Examiner* — Katrina Stransky
(74) *Attorney, Agent, or Firm* — James G. Passé; Passé Intellectual Property, LLC (57) ABSTRACT

The present invention relates to a device and method for cutting an annular piece out of the soft tissue of a selected mammal. The device can be utilized in surgical situations such as capsularhexis. The device comprises one or more blades which when rotated, cut an annular path.

4 Claims, 9 Drawing Sheets

(56) References Cited

U.S. PATENT DOCUMENTS

| | | | |
|---|---|---|---|
| 5,522,829 A | 6/1996 | Michalos | |
| 5,569,280 A | 10/1996 | Kamerling | |
| 5,728,117 A | 3/1998 | Lash | |
| 5,860,994 A * | 1/1999 | Yaacobi | A61F 9/00754 606/166 |
| 5,876,380 A | 3/1999 | Manganini et al. | |
| 6,066,138 A | 5/2000 | Sheffer et al. | |
| 6,165,190 A * | 12/2000 | Nguyen | A61F 9/013 606/166 |
| 6,306,155 B1 | 10/2001 | Chandler et al. | |
| 6,379,370 B1 | 4/2002 | Feinsod | |
| 6,551,326 B1 * | 4/2003 | Van Heugten | A61F 9/00754 606/113 |
| 7,122,042 B2 | 10/2006 | LoRusso | |
| 2004/0092982 A1 | 5/2004 | Sheffer | |
| 2005/0228419 A1 | 10/2005 | El-Mansoury | |
| 2006/0264990 A1 | 11/2006 | Michelson et al. | |
| 2006/0293648 A1 | 12/2006 | Herzon | |
| 2010/0241130 A1 * | 9/2010 | Deli | A61F 9/00754 606/107 |

OTHER PUBLICATIONS

Fisher et al., "Presbyopia and the Water Content of the Human Crystalline Lens", J. Physiol., 234, pp. 443-447, 1973.

Hodgson, "The Ultrasonic Scalpel", pp. 908-915, New York Academy of Medicine, pp. 908-915, May 8, 1979.

Krag et al., "Mechanical Properties of the Human Lens Capsule", Science Direct, Progress in Retinal and Eye Research 22, 2003, 2003 Elsevier Ltd., pp. 749-767.

Nagy et al., "Initial Clinical Evaluation of an Intraocular Femtosecond Laser in Cataract Surgery", Journal of Refractive Surgery, vol. 25, pp. 1053-1060, Dec. 2009.

Raviv, "The Perfectly Sized Capsulorhexis: Why we should strive to attain it", Cataract & Refractive Surgery Today, pp. 37-41, Jun. 2009.

* cited by examiner

APPARATUS AND DIAMOND BLADE MECHANISM TO MAKE AN ANNULAR INCISION IN SOFT TISSUE

This application is a Continuation-In-Part of U.S. non-provisional application Ser. No. 13/415,035 filed on Mar. 8, 2012, which claims priority of U.S. provisional application No. 61/450,389 filed on Mar. 8, 2011, and all are included herein in their entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to the surgical cutting of soft tissue. More particularly, the present invention relates to surgical devices and procedures that may require surgeons to perform annular cuts with precision in terms of position, size, and circularity.

Description of Related Art

One procedure in which it is useful to make an annular incision is capsulorhexis, an early step in cataract removal surgery. When performing capsulorhexis, an incision is made in the cornea, a tool is inserted into the eye through the incision, and a circular incision is made in the eye's lens capsule in order to gain access to the cataract. Although various devices have been created to perform this function, such as shown in US 2010/0241130 (Deli), there remains a need for a device that can perform annular incisions with precision in terms of position, size and circularity.

BRIEF SUMMARY OF THE INVENTION

In one aspect, a surgical device is provided for creating an annular incision in a soft tissue. The surgical device includes a cutting head comprising at least one blade and, in one embodiment, a pair of diametrically-opposed cutting blades and an actuator that induces mechanical motion of the cutting head such that the cutting blades follow an annular path about an axis of rotation.

In one embodiment, the blade is a diamond blade and, in one embodiment, the blade is V-shaped with a horizontal apex.

In another aspect, a method is provided for performing surgery on a soft tissue. The method includes actuating a cutting head to induce mechanical motion of the cutting head, such that one or more cutting blades follow an annular path about an axis of rotation. In some embodiments, the method further includes inserting the cutting head through an incision first made in a soft tissue before actuating the cutting head on a separate soft tissue.

In one embodiment, the invention includes a surgical device for creating an annular incision in the soft tissue of a mammal in a surgical procedure wherein the device comprises:
  a) a cutting head comprising at least one cutting blade and at least one axial arm with a blade attached to each distal end, and a proximal end of each arm joining at an axial rotation point: wherein the blades are straight and positioned such that when at least one arm is rotated circumferentially about the axial rotation point, the blades trace an annular cutting path; and
  b) a drive shaft coupled to the axial rotation point which in turn is connected to a crank open device rotation point and connected to a linear shaft at a second pivot point; and
  c) an actuator attached to the cutting head that causes the cutting head to rotate circumferentially about the axial rotation point.

DETAILED DESCRIPTION OF THE INVENTION

While this invention is susceptible to embodiment in many different forms, there is shown in the drawings, and will herein be described in detail, specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

The terms "about" and "essentially" mean ±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

References throughout this document to "one embodiment", "certain embodiments", and "an embodiment" or similar terms means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitations thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein, and use of the term "means" is not intended to be limiting.

As used herein, the term "surgical device" is a device designed for creating an annular incision in the soft tissue of a mammal (such as a human or a non-human animal) in a surgical procedure. The surgical device comprises a "cutting head" which is a device supporting one or more blades attached at a distal end or multiple distal ends that trace an annular cutting path. There can be a singular curved blade or a completely circular blade. In one embodiment, the blade is straight. One or more "axial arms" support each blade as shown in the drawings. The arms meet at an axial rotation point for spinning the blade(s) in an annular manner. The actuator is attached to the cutting head such that it causes the cutting head to rotate circumferentially about the axial rotation point such that the blades trace an annular path. Surgical devices for cutting an annular incision are well known (such as Deli, supra) although in one embodiment a novel device is described. None of the previous devices utilized diamond blades.

Surgical devices and procedures are provided in the present invention for making annular incisions in, for example, the soft biological tissues of a mammal. For another example, in an exemplary embodiment, the surgical device may be utilized in a cataract removal surgery, when performing capsulorhexis by first inserting a device through an incision made in the cornea. In other embodiments, the surgical device may be employed to make annular incisions in other types of soft biological tissue. Advantageously, in some embodiments, the cutting head of the surgical device may fit through a small incision (such as about a 3-5 mm long incision or less, or, in one embodiment, about 3-10 mm long incision or less) in a second outer tissue, be actuated to produce an annular incision in a first inner tissue, and then be removed from the tissue site through the incision in the outer tissue.

A surgical device is provided for creating an annular incision in a soft tissue. In one embodiment, the surgical device may include a cutting head comprising a pair of cutting blades located on the distal ends of the cutting head, and, in one embodiment, the blades are diametrically opposed i.e. positioned 180° apart on the two distal ends of the cutting head. In one embodiment, the surgical device may include a circular blade, and an actuator that induces mechanical circular motion of the cutting head such that, with the blades positioned at equal distances from the cutting head center axis, the cutting blades follow an annular path about an axis of rotation.

In certain embodiments, each of the cutting blades comprises a cutting edge that is arcuate in shape. For example, each of the cutting blades may have a cutting edge that projects toward a cutting surface in the shape of an arc. In other embodiments, the cutting edge projects toward the cutting surface in the form of a narrow cutting tip. The cutting edge may comprise any material suitable for cutting including, but not limited to, metal (such as stainless steel), diamond, or materials such as flexible metals such as nitinol. In one embodiment, the blade is diamond, having a lance or spear shape, and in a further embodiment, the apex of the blade is horizontal with lance side blades. It has been discovered that a diamond blade is far superior to other types of blades for circular cutting.

In some embodiments, each of the cutting blades is attached to at least one axial arm of the cutting head. For example, the cutting blades may be attached to a common connecting arm of the cutting head which acts as an axial arm for two blades. The axial arm(s) may be angularly rotated by a drive shaft, extending coaxially with the axis of rotation of the cutting head.

In some embodiments, the actuator comprises a crank arm operatively coupled to the cutting blades. For example, the crank arm may be attached to a drive shaft that extends coaxially with the axis of rotation of the cutting blades, such that the crank arm and drive shaft rotate in unison. In some embodiments, the actuator may further include a linear shaft operatively coupled to the crank arm such that linear movement of the linear shaft induces the cutting blades to follow the annular path. Such an actuating mechanism advantageously may overcome strength limitations of miniaturized gear systems. In other embodiments, the actuator may include a worm gear that drives a drive gear on the drive shaft. In other embodiments, the actuator may include a pulley drive system. For example, a continuous flexible cable may wrap around and drive a pulley or gear that is coupled to the drive shaft.

In some embodiments, the actuator is configured to induce an oscillation of the diametrically-opposed cutting blades along the annular path. For example, movement of the actuator may cause the diametrically-opposed cutting blades to alternately travel clockwise and counterclockwise directions along the annular path. Alternatively, the actuator may be configured to induce motion of the diametrically-opposed cutting blades in a single angular direction along the annular path. In one embodiment, the cutting head with two blades is rotated 180° to cut an annular hole.

In some embodiments, the cutting head is configured to be insertable through about a 3-5 or less mm long incision In one embodiment, it is configured to be insertable through about a 3-10 mm long incision. For example, the surgical device may include a hand piece and a wand extending between the hand piece and the cutting head. The cutting head may be positionable in an insertion configuration, in which the cutting blades are aligned with the wand. Thus, when the cutting head has two blades and is inserted through the incision, one cutting blade passes through the incision before the other cutting blade. In some embodiments, the cutting head is foldable or flexible to fit the incision, or sized to just fit the incision. In other embodiments, the surgical device may be utilized to cut tissue without inserting the cutting head through an incision.

In some embodiments, the hand piece further comprises a thumb slide operatively connected to the actuator such that motion of the thumb slide is translated into motion of the actuator. The thumb slide may be selectively positionable in a first position wherein the cutting head is positionable in an inserting configuration, and in which the diametrically-opposed cutting blades are aligned with the wand. The thumb slide may also be selectively positionable in a second position such that movement of the thumb slide between the first and second position induces motion of the cutting head. In another embodiment, the blades are motorized and rotate/oscillate based on activation of an electric power motor.

Figure 1:
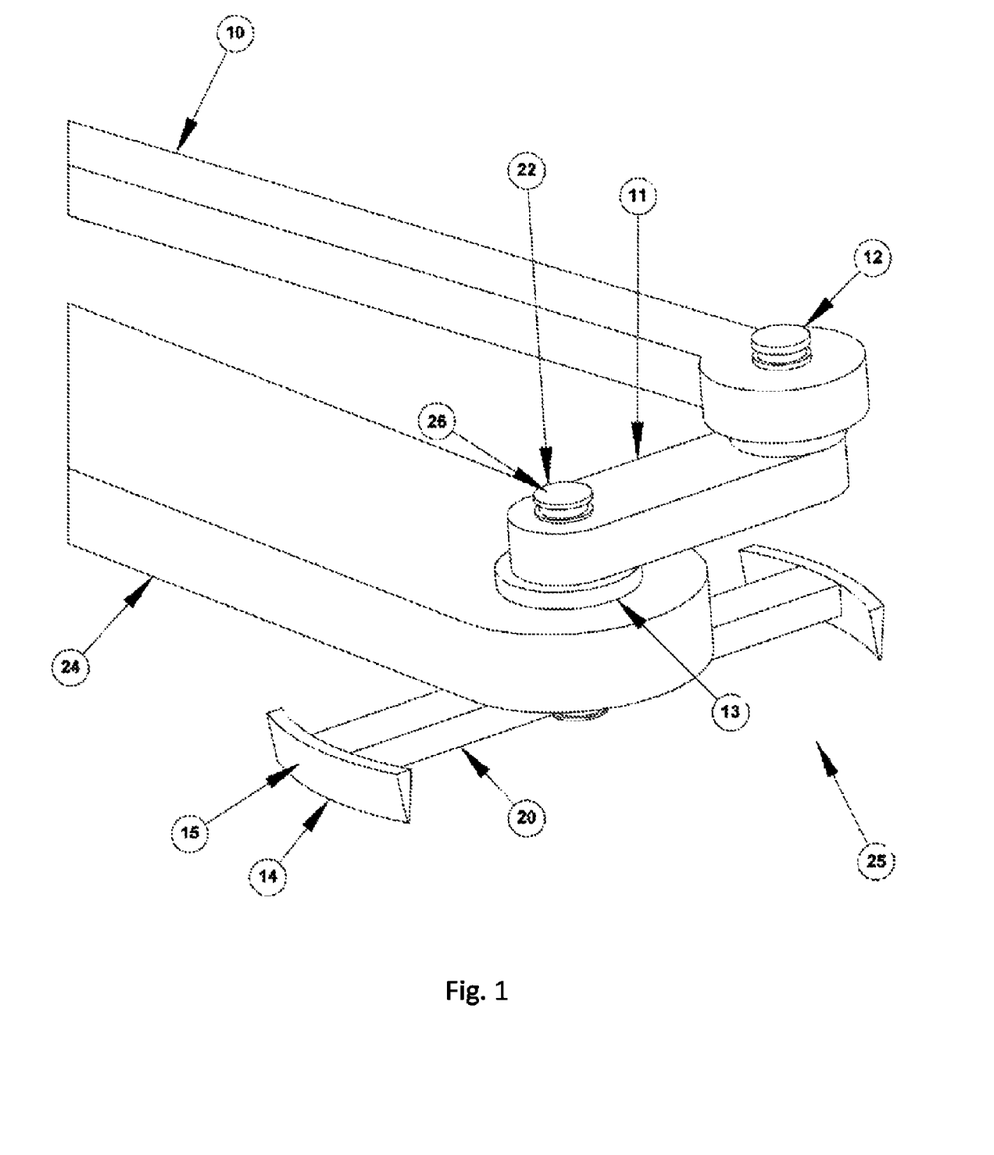
FIG. 1 is a perspective view of the rectangular-faced blade assembly on a cutting head of a surgical instrument constructed in accordance with one or more embodiments of the present invention.

FIG. 1 is a perspective view of an embodiment of a cutting head 25 for a surgical device. In the illustrated embodiment, each cutting blade 14 is arcuate in shape and has a rectangular face 15. The cutting blades 14 are attached at opposite ends of an axial arm 20 and these are diametrically-opposed and at equal distances from the rotation point 26. The axial arm 20 is coupled to a drive shaft 22 which passes through the wand 24. The drive shaft 22 at the axial rotation point 26 is connected to a crank arm 11 which is separated from the wand 24 with a bearing 13. The crank arm 11 is connected to a linear shaft 10 by a pivot joint 12.

Figure 2:
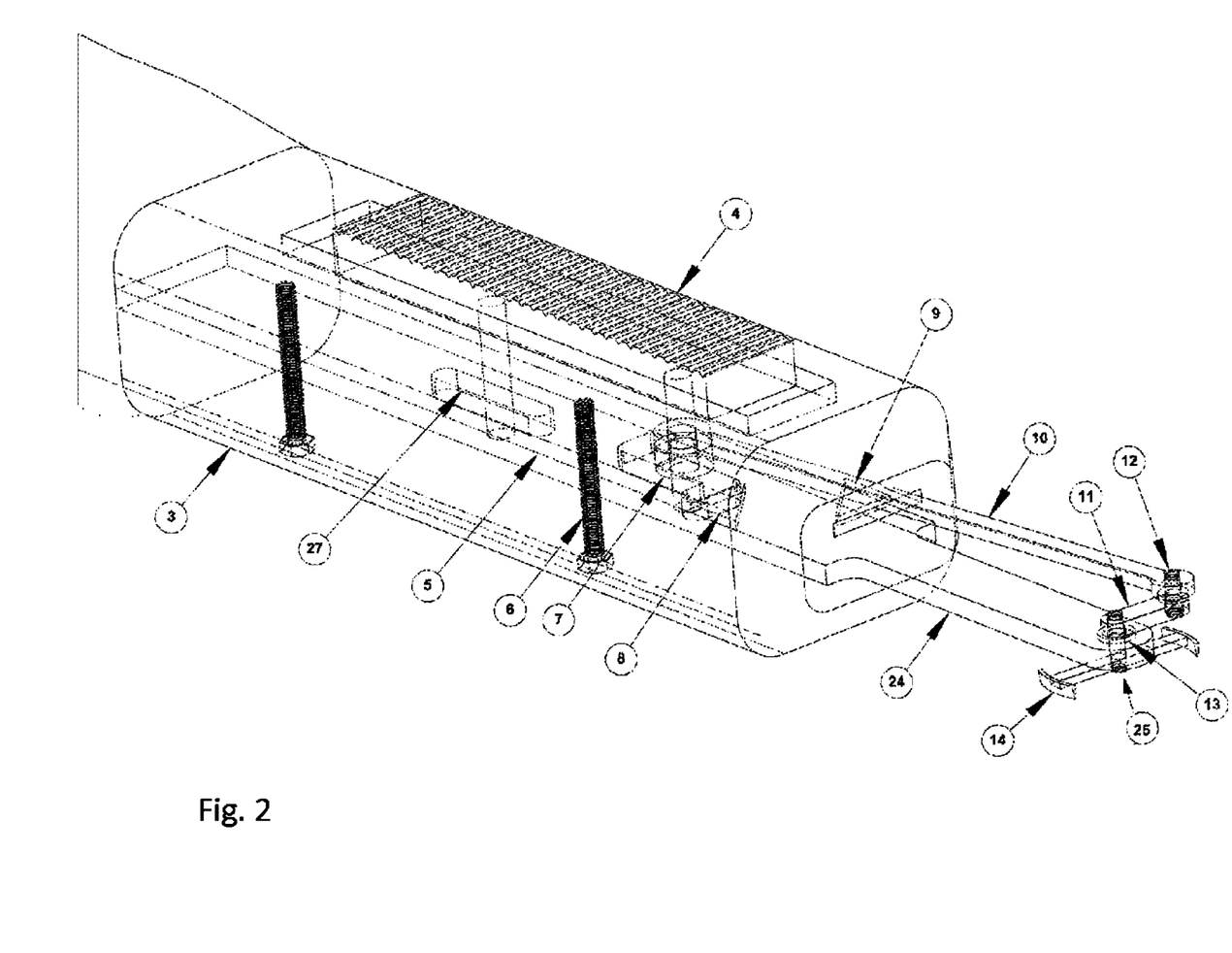
FIG. 2 is a perspective view of the front portion of a surgical instrument constructed in accordance with one or more embodiments of the present application.

As illustrated in FIG. 2, there is a perspective view of the surgical instrument. The cutting head 25 is attached at the end of a wand 24 that extends from a hand piece. The hand piece includes a housing 3 which houses at least a portion of the actuator (thumb slide) 4. The housing 3 also houses a guide plate 5 which guides the movement of the linear shaft 10. The guide plate 5 may be secured within the housing 3 by one or more fasteners 6. A thumb slide 4 is located on the outside of the housing 3 and is connected within the housing 3 to the linear shaft 10. The movement of the thumb slide 4 and the linear shaft 10 may therefore be constrained by the shape of a slot 27 provided in the guide plate 5. A bearing 7 may be positioned between the thumb slide 4 and the guide plate 5 to allow the thumb slide 4 to move freely along the guide plate 5 through the slot 27. In some embodiments, one or more bumpers 8 and/or a spring 9 may be employed to ensure that torque is applied to the cutting head in the desired direction when the linear shaft 10 and crank 11 are aligned in parallel.

Figure 3:
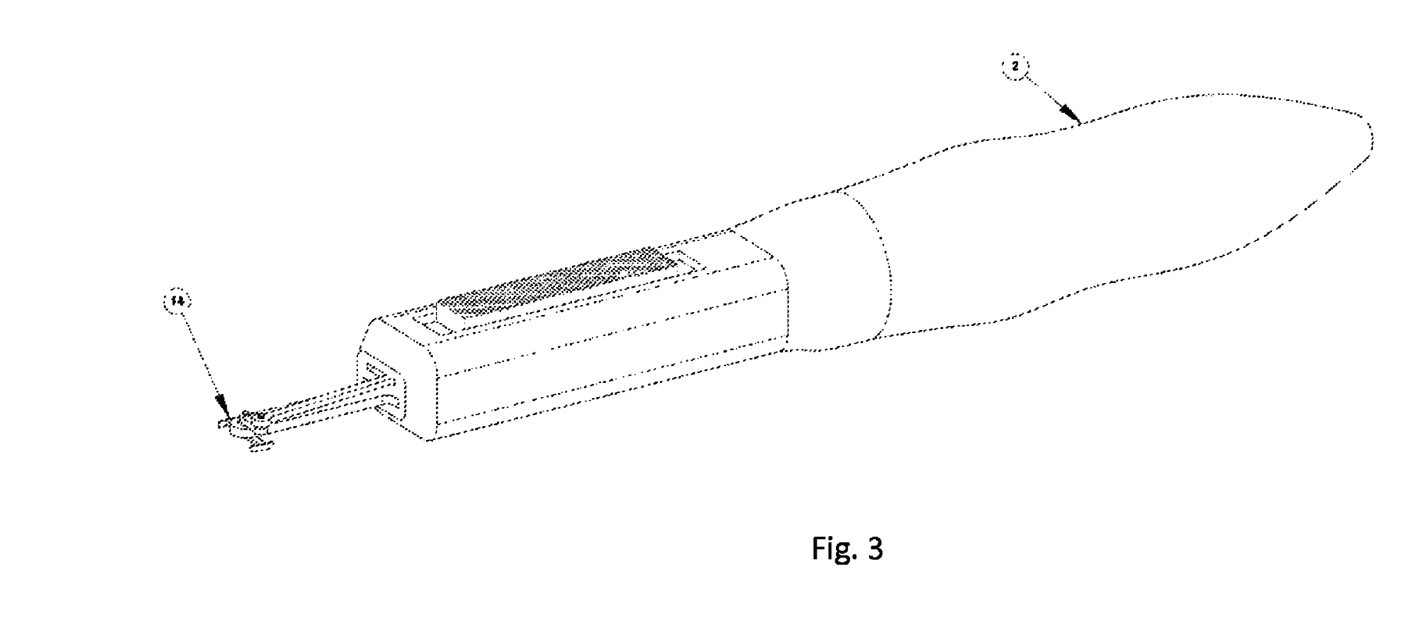
FIG. 3 is a perspective view of the surgical instrument of FIG. 1 and FIG. 2.

As illustrated in FIG. 3, the hand piece also includes a handle 2. The handle 2 may comprise a slip-resistant material. For example, the handle 2 may comprise a rubber or elastic material and/or may include tactile or gripping features. The housing may be made of any durable material, for example, ABS thermoplastic. The cutting blades 14, wand, connecting rod, linear shaft, crank arm, and thumb slide (as shown in FIG. 2) may be made of stainless steel or other appropriate material.

Figure 4:
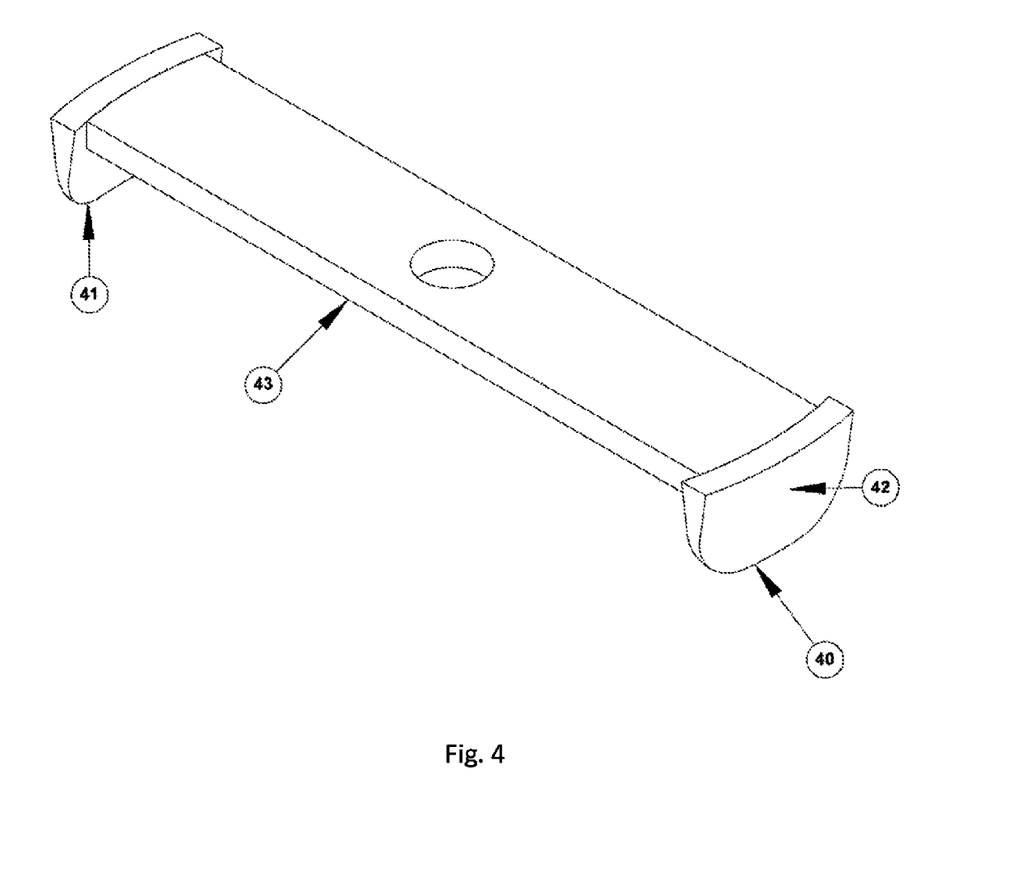
FIG. 4 is a perspective view of a broad blade-shaped blade face.
Figure 5:
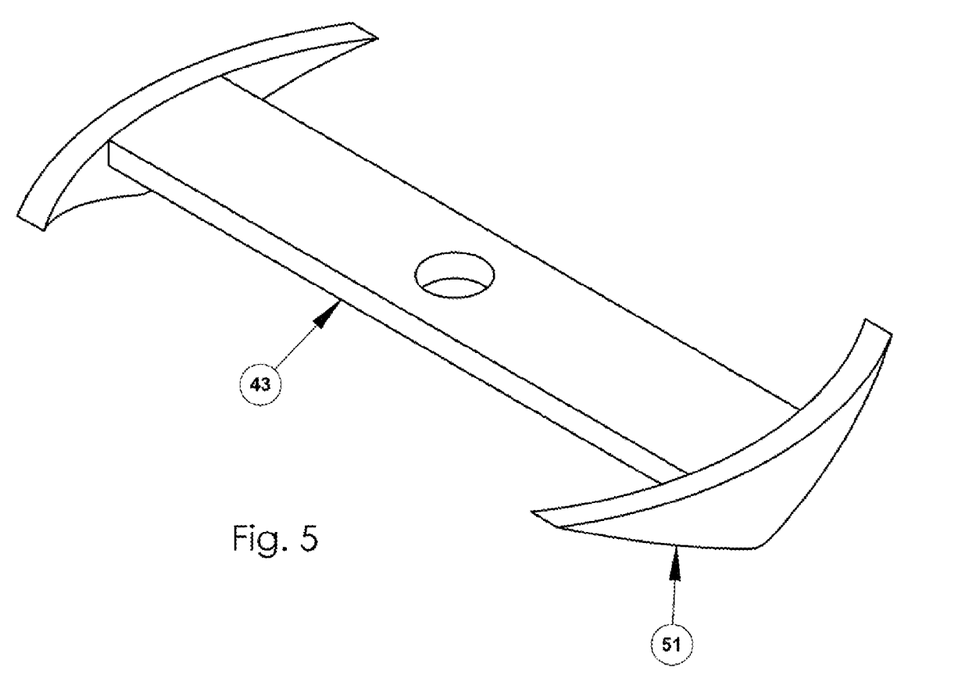
FIG. 5 is a perspective view of a triangular blade-shaped blade face.
Figure 6A:
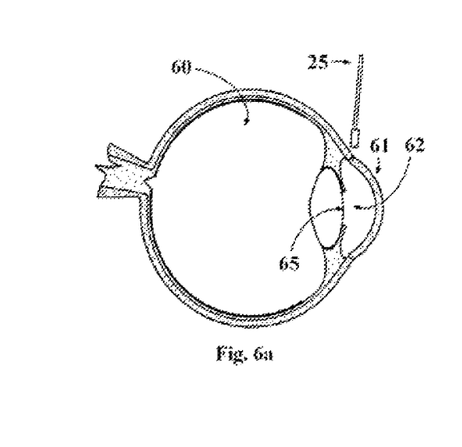
FIGS. 6a, 6b, and 6c are side views of the surgical procedure of the invention.
Figure 6B:
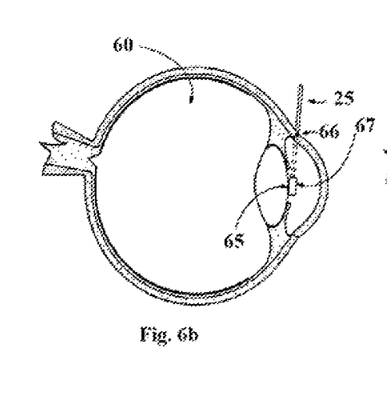
Figure 6C:
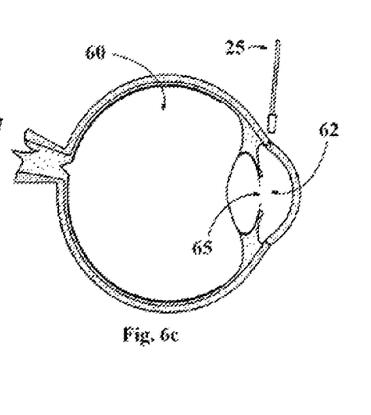

The surgical devices disclosed herein may be employed in various surgical applications. FIG. 4 is a perspective view of a set of dual blades 40 and 41 with a broad face 42 and arms 43. FIG. 5 is a perspective of a triangular blade face 51. For example, the surgical devices disclosed herein may be employed to produce annular incisions in various soft biological tissues including, but not limited to, ophthalmic tissue, cardiac tissue, uterine tissue, arteriovenous tissue, and dermal tissue. In an exemplary embodiment, the surgical device may be employed in a cataract removal procedure. For example, the surgical device may be employed when performing capsulorhexis. FIGS. 6a, 6b, and 6c depict respectively cutting head 25 approaching eye 60 ready to be inserted into cornea 61 to reach the aqueous humor 62 to reach lens 65. In FIG. 6b device 25 is inserted into incision 66 and blades 67 are placed against the capsule of the lens 65 and the tissue cut. FIG. 6c depicts the removed tissue and device 25 removed from the eye 60 at the end of the surgery.

When employed in a cataract removal procedure, the surgical device may be employed after an initial incision is made in the cornea. In some embodiments, the incision in the cornea may be relatively short, for example, about 3 mm. In other embodiments, the incision in the cornea may be as large as about 10 mm. The cutting head of the surgical device may then be inserted through this 10 mm incision and placed over the lens capsule. The cutting head may be placed at the desired location by aligning the drive shaft with the center of the region to be cut. The user may then actuate the thumb slide to make an annular incision. For example, the user may advance the thumb slide all the way forward, and then return the thumb slide to the original position. Once the thumb slide is returned to the original position, the annular incision may be complete and the cutting head may be removed from the tissue site through the corneal incision.

In the embodiment illustrated in FIG. 2, movement of the thumb slide 4 will cause the linear shaft 10 to move in the same direction as the thumb slide 4. The motion of the linear shaft 10 causes the crank arm 11 to rotate in a circular motion which will ultimately rotate the drive shaft and the cutting blades 14 attached thereto. In the illustrated embodiment, the bumpers 8 and spring 9, which is attached to the linear shaft 10, exert a force in a lateral direction relative to the direction of travel of the linear shaft at points of zero lever torque, ensuring continuous motion.

Figure 7:
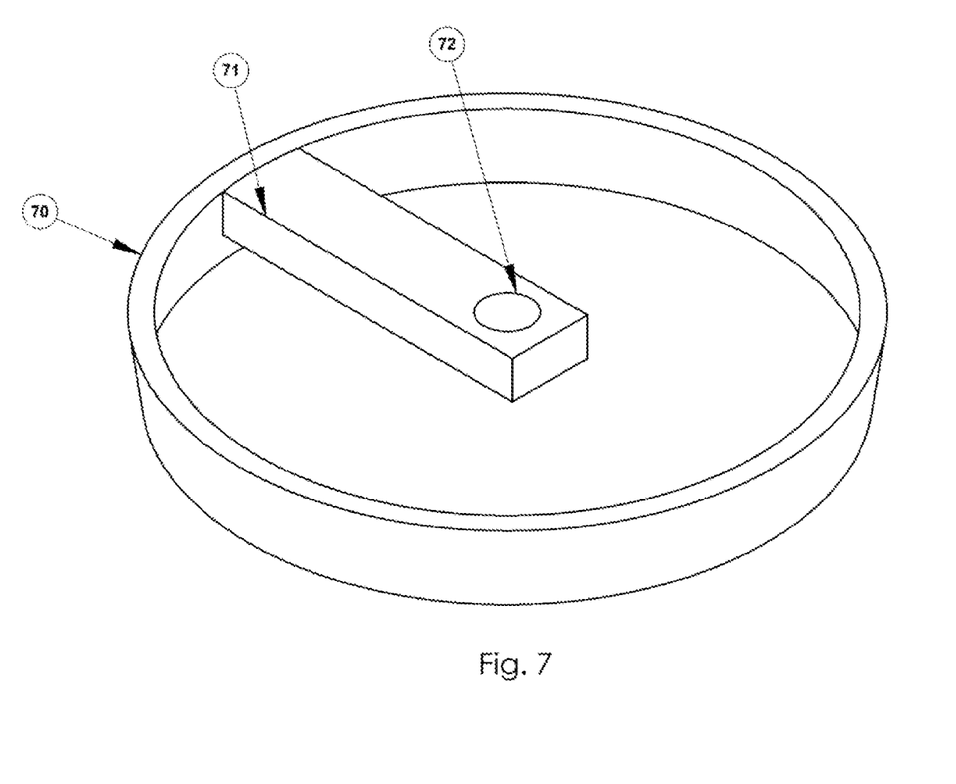
FIG. 7 is a perspective view of a circular blade of the invention.

In FIG. 7 there is shown a circular blade 70 having axial arm 71 and axial rotation point 72.

Figure 8:
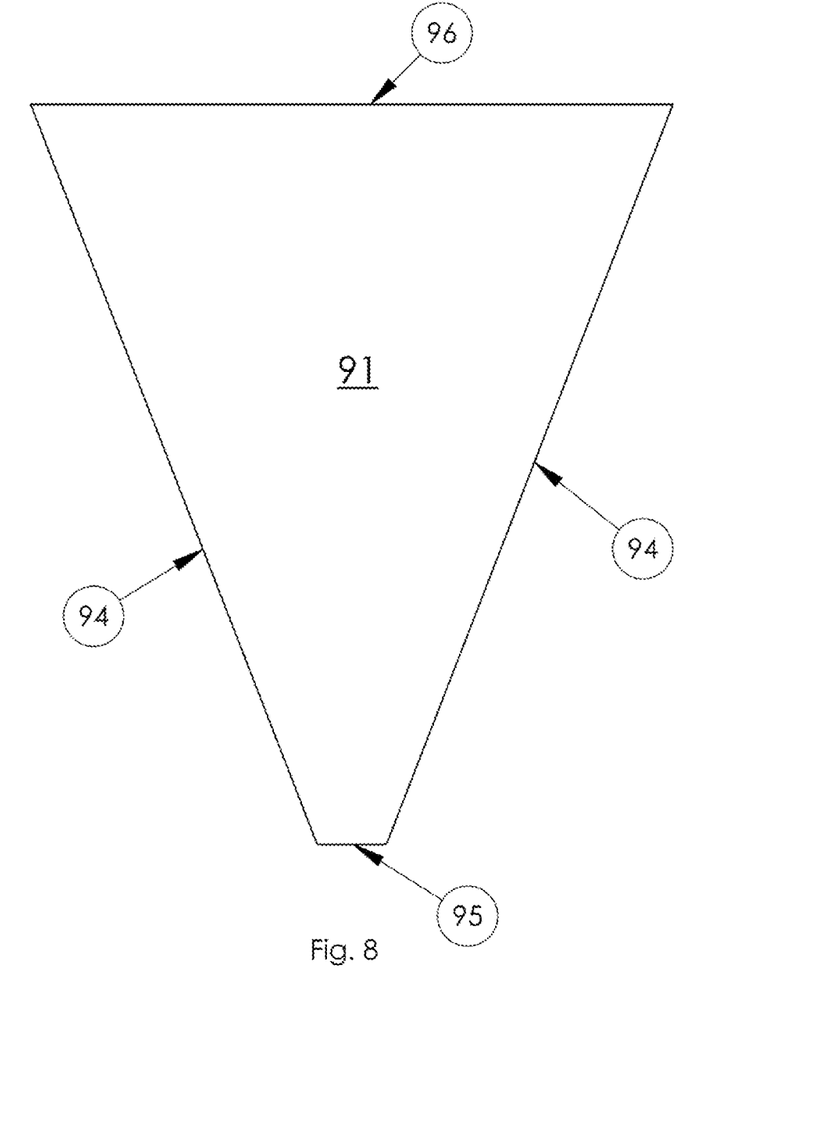
FIG. 8 is a view of a diamond blade of the invention.

FIG. 8 is a diamond cutting blade 91 having a lance shape with horizontal cutting edge 95 and side cutting edges 94. Edge 96 is fixably or foldably mounted to a distal end 85 of cutting arm 81 (seen in FIG. 9a).

Figures 9A, 9B, 9C:
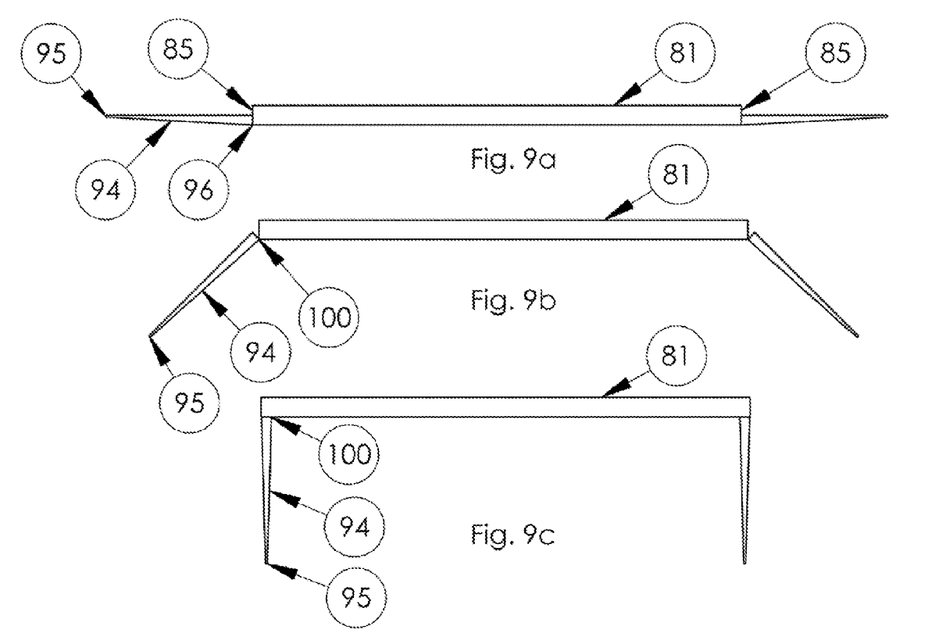
FIGS. 9a, 9b and 9c is a perspective view of diamond blades attached diametrically on a cutting head.

FIGS. 9a, 9b, and 9c are a side view of the diamond cutting blade, long foldable hinge 100 allowing the blade 91 to fold up and down in its attachment to cutting arm 81.

It should be apparent that the foregoing relates only to some embodiments of the present invention and that numerous changes and modifications may be made herein without departing from the spirit and the scope of the invention as defined by the following claims and equivalents thereof.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. A method of performing a surgical procedure on a first soft tissue of a mammal comprising cutting an annular piece of the first soft tissue, the method comprising:
   a) selecting a surgical device comprising:
      i. a cutting head comprising at least one cutting blade, the blades having a straight edge lance shaped side edge blade and at least one axial arm with a blade attached to each distal end, and a proximal end of each arm joining at an axial rotation point: wherein the blades are positioned such that when at least one axial arm is rotated circumferentially about the axial rotation point, the blades trace an annular cutting path;
      ii. a drive shaft coupled to the axial rotation point which in turn is rotatably connected to a first crank arm shaft at the rotation point and rotatably connected to a linear shaft at a second pivot point; and iii. an actuator attached to the linear shaft that causes the cutting head to rotate circumferentially about the axial rotation point by rotating the first crank arm shaft;

b) positioning the cutting blades against the first soft tissue in a position to cut the annular piece of tissue; and c) engaging the actuator to cut the tissue rotationally.

2. The surgical procedure according to claim 1 wherein the cutting head is inserted through a second soft tissue of the mammal in order to position the cutting blades against the first soft tissue.

3. The surgical procedure according to claim 2 wherein the procedure is capsulorhexis.

4. The surgical procedure according to claim 2 wherein the second soft tissue is the cornea of an eye.

\* \* \* \* \*